(12) United States Patent
Van de Velde

(10) Patent No.: US 6,186,628 B1
(45) Date of Patent: Feb. 13, 2001

(54) SCANNING LASER OPHTHALMOSCOPE FOR SELECTIVE THERAPEUTIC LASER

(75) Inventor: Frans J. Van de Velde, Boston, MA (US)

(73) Assignee: Jozek F. Van de Velde, Oosterzele (BE)

(*) Notice: Under 35 U.S.C. 154(b), the term of this patent shall be extended for 0 days.

(21) Appl. No.: 09/431,680

(22) Filed: Nov. 1, 1999

Related U.S. Application Data

(63) Continuation-in-part of application No. 09/317,098, filed on May 23, 1999, now abandoned.

(51) Int. Cl.[7] .................................................... A61B 3/10
(52) U.S. Cl. .................................................... 351/205
(58) Field of Search ............................ 351/200, 205–211, 351/221, 246; 600/310; 606/4, 5, 6

(56) References Cited

U.S. PATENT DOCUMENTS

| | | | |
|---|---|---|---|
| 5,815,242 | * | 9/1998 | Anderson et al. .................. 351/221 |
| 5,949,520 | * | 9/1999 | Heacock .............................. 351/221 |

* cited by examiner

Primary Examiner—George Manuel

(57) ABSTRACT

A combination of a scanning laser ophthalmoscope and external laser sources (52) is used for microphotocoagulation and photodynamic therapy, two examples of selective therapeutic laser. A linkage device incorporating a beamsplitter (56) and collimator-telescope (60) is adjusted to align the pivot point (16) of the scanning lasers (38, 40) and external laser source (52). A similar pivot point minimizes wavefront aberrations, enables precise focusing and registration of the therapeutic laser beam (52) on the retina without the risk of vignetting. One confocal detection pathway of the scanning laser ophthalmoscope images the retina. A second and synchronized detection pathway with a different barrier filter (48) is needed to draw the position and extent of the therapeutic laser spot on the retinal image, as an overlay (64). Advanced spatial modulation increases the selectivity of the therapeutic laser. In microphotocoagulation, an adaptive optics lens (318) is attached to the scanning laser ophthalmoscope, in proximity of the eye. It corrects the higher order optical aberrations of the eye optics, resulting in smaller and better focused applications. In photodynamic therapy, a spatial modulator (420) is placed within the collimator-telescope (60) of the therapeutic laser beam (52), customizing its shape as needed. A similar effect can be obtained by modulating a scanning laser source (38) of appropriate wavelength for photodynamic therapy.

6 Claims, 4 Drawing Sheets

SCANNING LASER OPHTHALMOSCOPE FOR SELECTIVE THERAPEUTIC LASER

CROSS REFERENCE TO RELATED APPLICATIONS

This U.S. application is a continuation-in-part of U.S. application Ser. No. 09/317,098, filed on May 23, 1999 and now being abandoned. It is further related to U.S. Pat. No. 5,923,399 issued on Jul. 13, 1999, U.S. Pat. No. 5,943,117 issued on Aug. 24, 1999 and U.S. Pat. No. 5,892,569 issued on Apr. 6, 1999.

BACKGROUND

1. Field of Invention

The invention relates generally to instruments and methods for examining and treating the eye and specifically to various kinds of ophthalmoscopes equipped with laser sources for the purpose of applying a therapeutic laser beam to the retina of an eye.

2. Description of Prior Art

Ophthalmoscopes, exemplified by the biomicroscope, are combined with a non-scanning therapeutic laser source for the purpose of retinal photocoagulation. Usually, a contact glass is placed on the cornea to be able to view the retina with the biomicroscope, and a mirror is used for reflecting the therapeutic laser beam onto the desired retinal location through a small part of the pupillary area. Importantly, the retina is illuminated with a strong visible light, and it is observed through different parts of the pupillary area to avoid reflexes, an arrangement that is known as Gullstrand's principle of ophthalmoscopy. Such optical configuration makes the art of precise focusing of a therapeutic laser beam on the retina more difficult. This is invariably the case in the presence of wavefront aberrations of the eye optics, a small pupil diameter, or a large diameter therapeutic laser beam. Vignetting of the external laser beam can possibly harm the anterior ocular structures.

To overcome the previous problems, U.S. Pat. No. 4,213,678, issued Sep. 29, 1980 to Pomerantzeff et al. discloses a co-pupillary scanning laser ophthalmoscope for the purpose of diagnosing and treating retinal disease using two different intensity levels of the scanning laser beam. One intensity range can be used for monochromatic imaging and angiography while a much higher level of the same laser beam or a different coaxial scanning laser beam is used for retinal photocoagulation. This novel approach however is not ideal because of the difficulties in implementing safety controls for such a scanning therapeutic laser beam, the difficulty in modulating the scanning laser beam over a range from non-coagulating to coagulating energies at video bandwidth, and the non-thermal complications of a high intensity pulsed laser beam in the nanosecond domain combined with an inappropriate duty cycle. Nevertheless, such a temporally modulated microphotocoagulation as proposed before by Birngruber and Roider, is useful to restrict the impact of the therapeutic application to the retinal pigment epithelium. However, an appropriate duty cycle is necessary and this cannot be achieved with a scanning therapeutic laser source as previously proposed; hence the necessity of an external non-scanning pulsed therapeutic source for this purpose.

Small, minimal intensity applications that are not pulsed and of longer duration, can more selectively target the photoreceptors through a combination of photochemical and thermal mechanisms of injury. These applications save functional retinal tissue in between them, and also these smaller spots can take a variability in absorption more easily into account. However, classic photocoagulating ophthalmoscopes have been limited in usefulness when such minimal intensity threshold laser is applied. One reason is that the anatomical changes caused by the therapeutic laser are often very difficult to visualize during the application in the presence of the photocoagulating light. The critical endpoint of such laser applications is often exceeded because the surgeon, upon recognizing the minimal anatomical changes within the retina, is also handicapped by a substantial human reaction time delay before s/he can interrupt the therapeutic laser. In addition, it is difficult to permanently document selective therapeutic laser applications on the retinal image because both threshold and pulsed applications are typically not visible a short time after the delivery.

U.S. Pat. Nos. 5,923,399, 5,943,177 and 5,892,569 to Van de Velde address these problems and they describe different embodiments of a confocal scanning laser ophthalmoscope that is optimized for delivering selective therapeutic laser of various nature to the retina. This includes temporally modulated applications, small threshold continuous applications and applications that use a photosensitizer drug. The latter method is called photodynamic therapy, similar to transpupillary thermal therapy without the dye injection, and typically uses long duration, larger circular applications of laser light that is preferentially absorbed by the photosensitizer drug. It aims at selectively closing abnormal small blood vessels within or underneath the retina.

OBJECT, SUMMARY AND ADVANTAGES OF THE INVENTION

One object of this invention is to describe additional embodiments of the confocal scanning laser ophthalmoscope optimized for delivering selective therapeutic laser to the retina. These additional embodiments improve the spatial selectivity of such therapeutic laser applications. This goal is accomplished by taking into account the basic principles of coupling external laser sources with the scanning laser ophthalmoscope as outlined in previous disclosures, further incorporating two new features for spatially modulating small applications in microphotocoagulation and larger applications in photodynamic therapy. The first method aims at neutralizing the measured wavefront aberrations of the human eye with the help of an adaptive lens, according to the technique of Navarro and Moreno (ARVO meeting 1999, Optics Letters, 2000). The adaptive lens is fixed to the scanning laser ophthalmoscope and situated as close as is possible to the cornea of the subject. Aforementioned U.S. Pat. No. 5,943,117 describes an embodiment of the confocal scanning laser ophthalmoscope that is capable of analyzing the complex wavefront aberrations of the human eye. That information is used to manufacture the adaptive lens and thus to obtain even more selective, smaller therapeutic applications within the retina, possibly diffraction limited. The second method describes how to spatially modulate the circular shape of a larger therapeutic laser application as in photodynamic therapy. A mask of appropriate contour, corresponding to the lesion or protecting a specific area, is positioned in the focusing collimator-telescope, at a retinal conjugate plane. Another object of this invention is a re-evaluation of the feasibility to use a scanning laser as the therapeutic source of photodynamic therapy.

REFERENCE NUMERALS IN DRAWINGS

Figure 1:
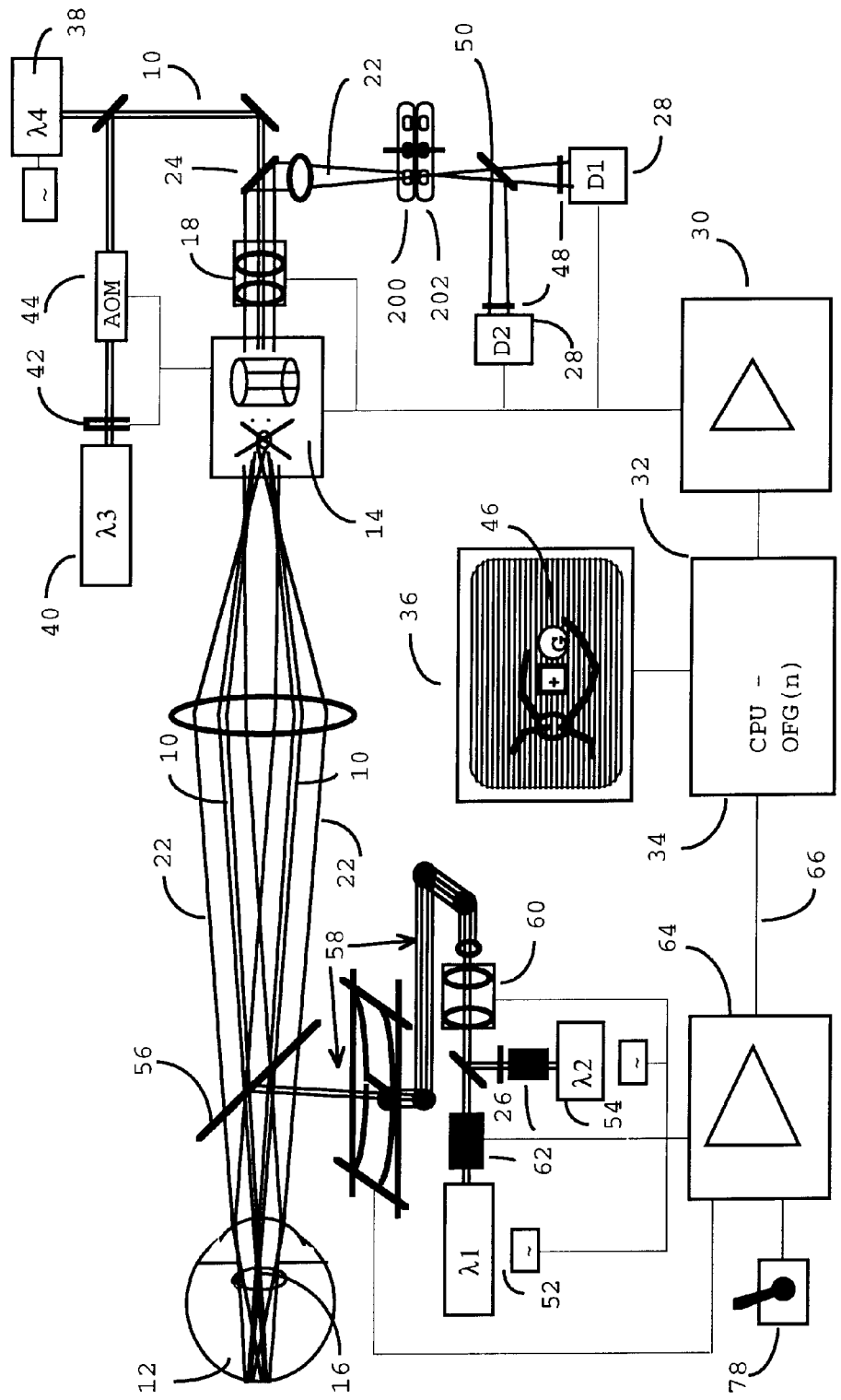
FIG. 1 is a representation of prior art, illustrating the different components of a generic confocal scanning laser ophthalmoscope that is optimized for the delivery of therapeutic laser to the retina. Three parts can be distinguished. (1) A confocal scanning laser ophthalmoscope. (2) Two external therapeutic and diagnostic non-scanning lasers with different temporal modulation options, coupled with the scanning laser ophthalmoscope using an optimized beamsplitter and separate telescopic device. (3) The computer with one or more linked overlay framegrabber graphic cards, capable of advanced digital image processing.

10 Gaussian beams of laser light of scanning laser ophthalmoscope
12 Posterior pole of the eye, retina
14 Scanning optics of scanning laser ophthalmoscope
16 Similar Maxwellian view of scanning and therapeutic beams, common pivot point
18 Collimator-telescope for scanning laser beams of ophthalmoscope
20 Lens changes causing optical aberrations in the media of the eye
22 Backscattered light returning from the retina
24 Beamsplitter or aperture for separation of the backscattered laser light
26 Combining beamsplitter, optionally polarizing
28 Avalanche photodiode detectors
30 Video and sync generating electronics of scanning laser ophthalmoscope
32 Computer
34 Overlay frame grabber graphic card(s)
36 Video display monitor
38 SLO laser for imaging purposes, $\lambda 4$, e.g. 792 nm
40 SLO laser for microperimetric purposes, $\lambda 3$, e.g. 632, 532 nm
42 Pair of adjustable linear polarizers, attenuator
44 Acousto-optic modulator
46 Overlay on retinal image indicating area illuminated by the therapeutic laser
48 Barrier and polarizing filters, interference filters
50 Beamsplitter for separating scanning and external laser light
52 External, non-scanning therapeutic laser, $\lambda 1$, e.g. 689 or 532 nm
54 Second wavelength external laser source, $\lambda 2$, e.g. 635 nm or 685 nm
56 Beamsplitter combining light from scanning and external laser sources
58 Optional opto-mechanical linkage device with variable degrees of freedom
60 Collimator-telescope for external therapeutic laser beams
62 Safety shutter, acousto-optic modulator, or mechanical chopper
64 Electronic circuitry for elements 52, 54, 58, 60, 62
66 I/O link between supporting electronics 64 and computer
78 Joystick-micromanipulator for moving the fixation target and microperimetry
200 First confocal aperture
202 Second optional confocal aperture
300 Optic fiber, either low or high N.A.
306 Polarizer
308 Mechanical transducer for coherence reduction, optional pulsing of beam
318 Adaptive lens, capable of correcting higher order aberrations
400 Conjugate or confocal retinal planes, plane of spatial modulator
410 Conjugate or confocal plane of light sources and pivot point
420 Spatial modulator, simple transparency mask or liquid crystal technology
430 Transparent part of spatial modulator, bandpass for $\lambda 1$ and $\lambda 2$
440 Opaque part of spatial modulator for $\lambda 1$ and $\lambda 2$

DETAILED DESCRIPTION AND OPERATION OF PREFERRED EMBODIMENTS

Figure 2:
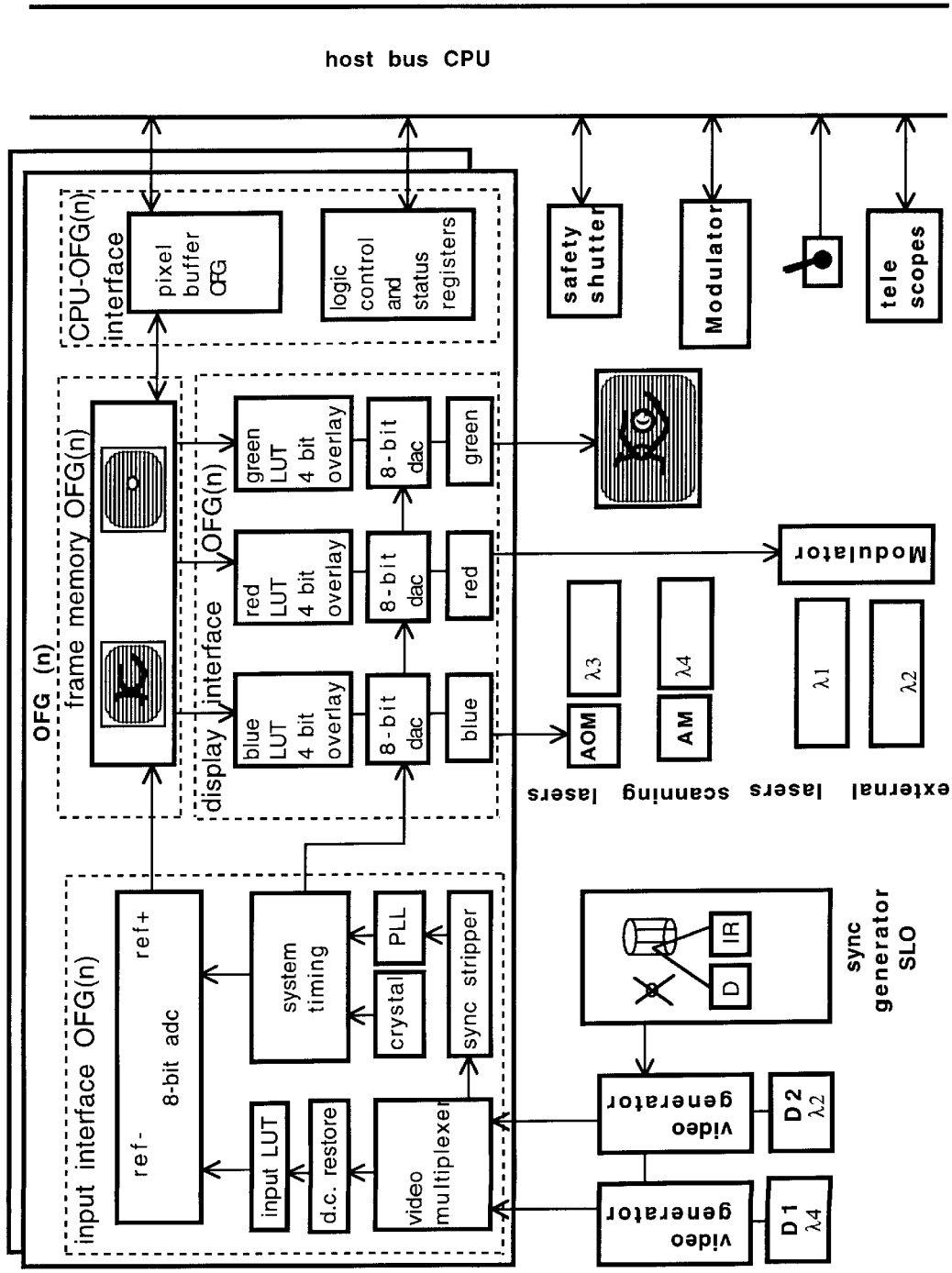
FIG. 2 shows a prior art block diagram of an overlay frame grabber card capable of such advanced image processing. The overlay frame grabber graphic card(s) have an input interface, frame memory, display interface and CPU interface. Besides the OFG cards, the host bus accommodates a I/O for interaction with several components of the therapeutic laser assembly and telescopic focusing device. Electronic pathways include: (1) a synchronized video-in pathway from the SLO detectors. (2) a video-out pathway to monitor and laser modulators. (3) a system timing generator with genlocking of the other components of the board.
Figure 3:
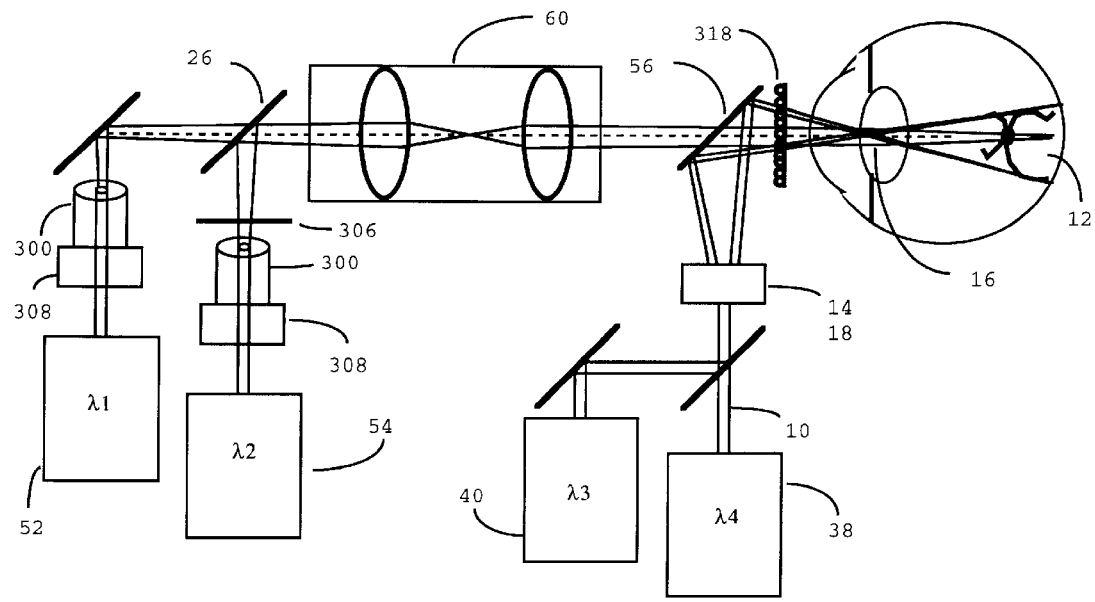
FIG. 3a details the ray tracing of the external therapeutic or aiming diagnostic laser beams. A common pivot point with the lasers of the confocal scanning laser ophthalmoscope is a key feature. A new optical element, situated in front of the eye but fixed to the scanning laser ophthalmoscope, corrects for higher order aberrations. The position of this lens is adjustable.
FIGS. 3b,c show the ray tracing before and after correcting for such higher aberrations.
Figure 3:
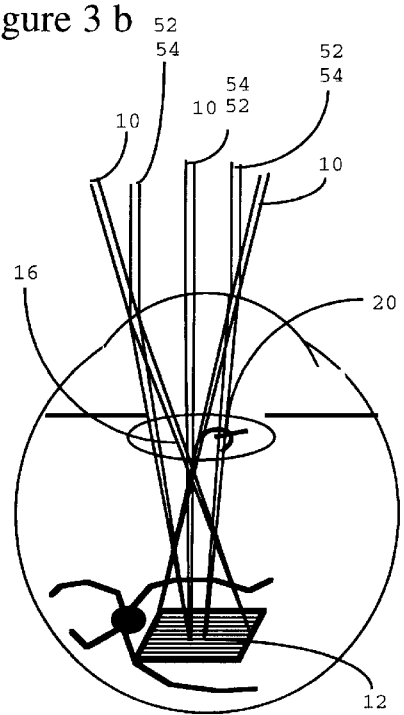
Figure 3:
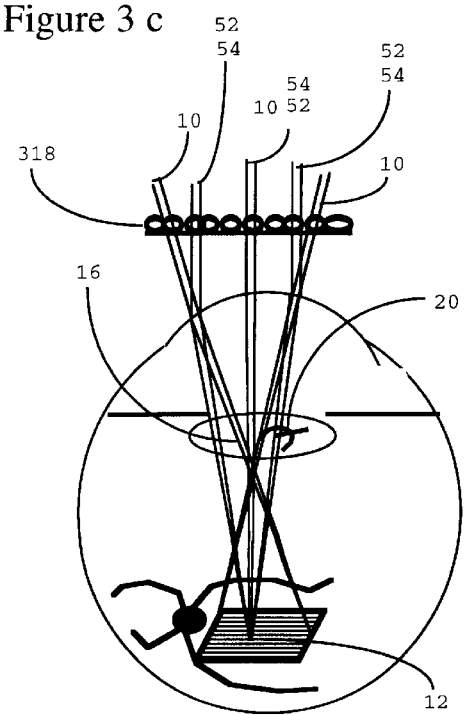
Figure 4A:
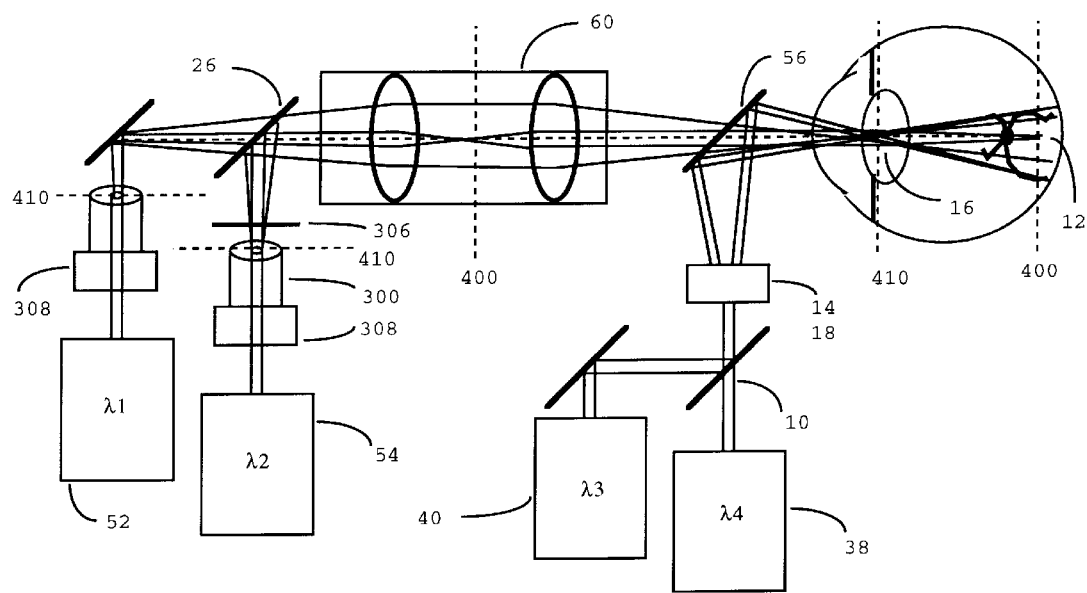
FIG. 4a shows the ray tracing of the external therapeutic or aiming diagnostic laser beams. A common pivot point with the lasers of the confocal scanning laser ophthalmoscope prevents vignetting, and results in a minimal aberration of the beams and predictable focusing on the retina. A new feature is the introduction of a spatial modulator for the collimated and large diameter laser beams within the focusing telescope optics. The mask plane is conjugate with the retinal plane. Additionally, coherence and mode propagation is decreased in the retinal spot with the help of a mechanical transducer.
Figure 4B:
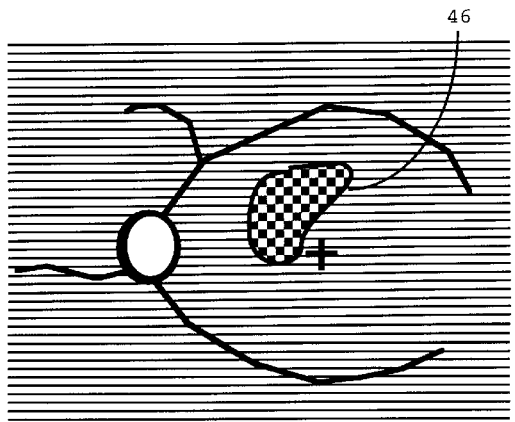
FIG. 4b illustrates the outline of a retinal lesion. The corresponding mask in the spatial modulator is shown in FIG. 4c.
Figure 4C:
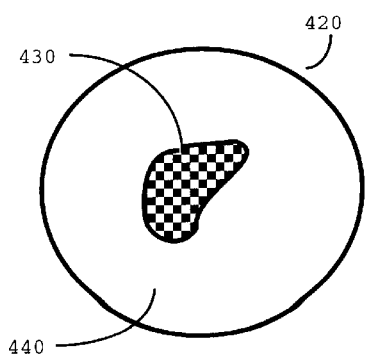

An embodiment of the confocal scanning laser ophthalmoscope for delivery of therapeutic laser to the retina is illustrated in FIGS. 1 and 2 (Van de Velde). The principles of scanning laser ophthalmoscopy are described in detail in the prior art (Pomerantzeff, Saban, Webb). Two additional possibilities for spatial modulation of therapeutic lasers are illustrated in FIGS. 3 and 4.

I. Summary of Prior Art

A confocal scanning laser ophthalmoscope (cSLO) can be optically coupled with multiple external diagnostic or therapeutic laser sources 52, 54 with the help of an appropriate beamsplitter 56. For cSLO imaging, an infra-red diode laser 38 e.g. 792 nm or 830 nm is preferred. For cSLO psychophysics and microperimetry a visible wavelength e.g. 532 nm or 633 nm laser 40 is convenient. The 532 nm wavelength has a superior visibility, especially during photodynamic therapy employing 664 nm or 689 nm laser light. Microphotocoagulation and photodynamic therapy use various wavelength sources 52 between 532 nm and 830 nm. Usually, an aiming beam 54 of different wavelength is necessary. The retractable beamsplitter 56 has to be optimally reflective for the therapeutic wavelength, semitransparent for the aiming beam wavelength, variably transparent for the psychophysical wavelength of the cSLO and highly transparent for the imaging wavelength of the cSLO. E.g. if λ4 is 792 nm, λ3 is 532 nm, λ2 and λ1 are equal to 690 nm, then the Melles-Griot long-wave pass beamsplitter 03BDL can be used. To realize this coupling of lasers, several advanced principles have been implemented in previous disclosures.

A The opto-mechanical linkage device primarily adjusts the position of the pivot point 16 of the scanning laser beams 38, 40 as to coincide with the pivot point 16 of the non-scanning external therapeutic laser beams 52, 54. Optimizing the Maxwellian viewing of a retinal location with the cSLO will then result in a minimal optical distortion and attenuation of the external laser beams, because the same optical pathway is used. Also in this situation, the amount of prefocusing necessary to image on the retina is a reference, if needed, for focusing the therapeutic laser beam 52 with its proper telescopic optics 60. This configuration also eliminates the danger of vignetting and hitting inadvertently the iris with the therapeutic laser 52, a consideration of particular importance in photodynamic therapy.

B As mentioned before, an external diagnostic laser source 54 can be used for the quantification of wavefront aberrations or Stiles-Crawford parameters of the eye optics when it is scanned in parallel fashion across the anatomical pupil of the eye. Gaussian and small diameter beam profiles are preferred as they produce a relatively small spot on the retina, with a large depth of focus. VCLES are here of increasing interest. An array of about 60 computer modulated cylindrical $In_{0.2}Ga_{0.8}As$ surface-emitting quantum-well laser diodes with lasing wavelengths in the vicinity of 970 nm and shorter can substitute the external diagnostic laser source 54 together with the translational movement of the pivot point 16. A collimator-telescope, e.g. made of a selfoc planar microlens array material, adjusts the spacing and alignment of the individual laser beams. The position of their corresponding spots on the retina can be determined on the retina. With the help of Zernike polynomial analysis the wavefront aberration coefficients can then be calculated.

C A co-pupillary scanning laser ophthalmoscope cannot be used to detect the impact of the external laser beam 52, 54 on the retina. The confocal instrument can do this, however in a limited fashion. The SLO image of the external laser spot on the retina actually results from a convolution of the stationary real laser spot with the flying confocal detection aperture 200 in the cSLO. Often, the confocal aperture 200 of the scanning laser ophthalmoscope is significantly larger than the actual laser spot. Therefore, the latter's location but not its size or focusing can be precisely determined by observation alone. A combination of confocal apertures 200 and 202 has been proposed to solve the problem. This is not an absolute requirement since it is possible to calculate the approximate size of the spot on the retina. This size can be shown on the retinal image as a semi-transparent overlay or outline 46.

D Although it is possible to realize the foregoing with one detector 28, considerable advantages are derived from using two detectors 28 that are temporally synchronized. Using the appropriate beamsplitter 50 and filters 48, one detector 28 images the retina and the anatomical changes caused by the therapeutic laser with infra-red light, unimpeded by the therapeutic laser light. A second and synchronized detector 28 receives only the backscattered light from the external aiming laser beam 54, without the disturbing background of moving retinal details. This backscattered light is localized in its video image with imaging hardware 32, 34. The use of two detectors 28 allows the registration of therapeutic laser applications on the retinal image, tracking, and the activation of a safety shutter in case of excessive misalignment.

E The aiming beam 54, which is usually of a wavelength different from the therapeutic laser source 52, is polarized. Its light is partially transmitted after backscattering from the retina through the beamsplitter 56. Only the aiming beam wavelength is allowed to reach one of the photo-detectors 28, where a polarizer-analyzer 48 further represses the corneal reflections that may otherwise appear as a second confusing spot or veiling on the retinal image. After appropriate image processing with a computer 32 and graphics card 34, an outline or transparent overlay 46 indicates size, shape and position of the corresponding therapeutic application.

F Pulsing of the aiming beam 54 permits higher but still safe peak power to be used. This is advantageous to counter losses in the presence of small confocal apertures, filters, beam splitters, and polarization of the aiming beam. Pulsing of the aiming beam 54 requires anti-aliasing relative to its confocal detection on the retina.

II. Advanced Spatial Modulation Options for Selective Therapeutic Laser

A In a previously discussed embodiment of a scanning laser ophthalmoscope that is optimized for microphotocoagulation, an optional aspheric lens was proposed, positioned on the anterior surface of the cornea. This lens is useful to reduce higher order wavefront aberrations, mainly caused by irregularities in the anterior surface of the cornea. Comparable solutions, using adaptive optics involving deformable mirrors, have also been proposed before by Williams (U.S. Pat. No. 5,777,719) for use with the scanning laser ophthalmoscope. These mirrors have the advantage of adapting to the wavefront aberrations dynamically in real-time. However, they control only the scanning beams 38, 40 of the scanning laser ophthalmoscope. In order to correct the raytracing of both external therapeutic lasers 52, 54 and scanning lasers 38, 40, an additional lens is needed between the eye and the ophthalmoscope. Such correcting lenses have been proposed as a contact lens since Smirnov (Biophysics 1962). They will move with the eye in different directions of gaze and are therefore advantageous. However they usually rotate as well, making them useless when their anterior surface is not symmetric around the visual axis. A non-contact correcting lens 318 should therefore be calculated from raytracing data and constructed to be fixed onto the scanning laser ophthalmoscope and not onto the eye. This configuration allows the lens 318 to be brought close to the eye, at the same time selecting a particular entrance location 16 for the different laser beams, and controlling the direction of gaze of the subject with a fixation target created by the diagnostic laser beam 40 and modulator 44. To some degree, it would still be necessary to construct different lenses 318 for different entrance locations 16 of the beams inside the eye. The economical manufacturing of such an individualized lens 318 has been reduced to practice by Navarro et Al. (ARVO, 1999). Examples are the etching of plastic substances with excimer lasers, or recently, the UV photosculpting of photoresist coated optical components.

B A therapeutic laser 52 can be used in association with absorbing dyes. In photodynamic therapy, a photosensitizing drug, e.g. Verteporfin from CibaVision, is first injected and laser light of an appropriate wavelength, e.g. 689 nm, is then applied with the aim of creating a chemical reaction that closes off small and abnormal blood vessels; incidentally, this opens the possibility to apply in a second stage conventional 532 nm laser to penetrate more completely in deeper layers of the retina or to close so-called feeder vessels more easily because the blood flow has been halted or considerably reduced. The normal procedure however is to wait and see over a period of three months whether the abnormal blood vessels remain closed. An average of 3 to 4 treatments seem to be necessary to obtain this goal. In conventional photodynamic therapy, the following parameters are routinely used for the therapeutic laser source 52. A fluency of 50 J/sq. cm corresponds to a power output of 600 mW/sq. cm for an application duration of 83 seconds. The circular spot size can be as large as 4000 $\mu$ in diameter to cover the lesion completely. Nevertheless, this is still easy to deliver with a diode laser of 300 mW power output and a larger N.A. fiber optic delivery system. In conventional delivery systems using a slitlamp and eye contact glass, a circular aiming beam of separate wavelength e.g. 650 nm is necessary. Only a number of discrete circular treatment diameters are provided and there is only a minimal control of the subject's fixation.

Photodynamic therapy with the SLO benefits from a superior infra-red imaging that better outlines the areas to treat on a monitor 36. Especially subretinal neovascularization and discrete areas of retinal swelling can be detected, often without the need for injection of angiographic dyes. Furthermore, the SLO permits a microperimetric evaluation of the lesion with the same instrument. Fixation characteristics and absolute thresholds are useful for treatment decisions and follow-up. SLO potential acuity values, measured under bright background conditions, are a predictor for the outcome of photodynamic therapy. The use of the scanning laser ophthalmoscope as a delivery system permits a non-contact technique with superior control of fixation. Patients that are going to receive photodynamic therapy can usually still fixate under bright photopic conditions, thereby allowing the location of the therapeutic spot to be adjusted with the help of the fixation target and not necessarily by moving the spot. Therefore, the linkage device can be considerably simplified, obviously still making sure that the pivot points 16 of SLO lasers 38, 40 and therapeutic laser 52 are similar in location as much as possible.

Because of its interfacing with a computer 32, digital framegrabber 34 capable of overlay programming, and possibility of fixation control, the scanning laser ophthalmoscope does not need a separate wavelength aiming beam 54 for photodynamic therapy. The position and extent of the therapeutic spot can be stored as an overlay 46 before any injection of photosensitizer dye, using a well-defined location of the fixation target and an approximate constant entry position 16 of the laser beams. The long duration and one-time application can be planned before the injection of the dye. For this purpose, the external therapeutic beam 52 at low power setting and polarizer 306 are sufficient. Also, one detector 28 equipped with a removable barrier filter 48 for the therapeutic light is adequate for the same reasons.

An improved embodiment employs a spatial modulator 420 that is associated with the focusing collimator-telescope 60 of the therapeutic laser beam 52. The geometrical optics are simple. First, the divergent therapeutic laser light 52 is collimated by a first element of the focusing means 60, then it passes through the spatial modulator 420, and then it is further focused onto the retina by a second element of focusing means 60, using the same pivot point 16 as the scanning laser ophthalmoscope. The easiest way to obtain this configuration is to have the exit aperture of the optic fiber 300 and pivot point 16 in conjugate planes 410, and the posterior pole of the retina 12 and spatial modulator 420 in conjugate planes 400. Other configurations can be envisaged as well and are within the scope of conventional matrix optics raytracing, e.g. with regard to the positioning of beamsplitter 56 relative to the SLO optics, and movement of the mask 420. The spatial modulator 420 can be very simple. For example, consisting of a transparent area 430 for the therapeutic light 52, of any shape, surrounded by a barrier area 440 for the therapeutic light. The shape can be determined and created on forehand, using a mock-up treatment session with all variables such as fixation known. It can be printed out on a transparency with the help of a laser writer. More sophisticated masks employing liquid crystal technology can change in real-time under computer 32 control. The capability of spatially modulating the area to treat is particularly important in the event of re-treatments where one may wish to protect the foveal fixation zone, potential fixation areas or horizontal meridian. It would also spare healthy tissue during the initial treatment session.

It is advantageous to apply a high frequency vibration with transducer 308 to the optic fiber 300 carrying the therapeutic laser light 52. This is one method for reducing coherence and mode propagation when dealing with larger spot sizes of longer duration on the retina. Also, it may be necessary to smooth out a broader unevenness in therapeutic light distribution, for example with a gradient neutral density filter. This can be accomplished at a retinal conjugate plane.

C As mentioned before, U.S. Pat. No. 4,213,678 to Pomerantzeff et al. discloses a co-pupillary scanning laser ophthalmoscope for the purpose of diagnosing and treating retinal disease using two different intensity levels of the scanning laser beam. One intensity range can be used for monochromatic imaging and angiography while a much higher level of the same laser beam or a different coaxial scanning laser beam is used for retinal photocoagulation. This novel approach however is not ideal because of the difficulties in implementing safety controls for such a scanning therapeutic laser beam, the difficulty in modulating the scanning laser beam over a range from non-coagulating to coagulating energies at video bandwidth, and the non-thermal complications of a high intensity pulsed laser beam in the nanosecond domain combined with an inappropriate duty cycle.

Photodynamic therapy has until now been performed with continuous output lasers. Van de Velde proposed in U.S. Pat. No. 5,892,569 to use the pulsed microperimetric stimulus of the scanning laser ophthalmoscope for this purpose, at the appropriate wavelength and intensity level because photochemical, rather then thermal mechanisms are responsible for its action on the target tissue. As a practical example, Verteporfin from CibaVision is excited at 689 nm. A fluency of 50 J/sq. cm equivalent to 600 mW/sq. cm is needed for about 83 seconds. Current delivery systems incorporate a diode capable of emitting at least 300 mW at this wavelength, thus in theory it is also possible to cover about 0.5 sq. cm with the scanning laser ophthalmoscope. Recently, we demonstrated that a fluency distribution of 600 mW/sq. cm for 83 s of continuous delivery, is approximately equivalent to 0.5 $\mu$W/sq. 10 $\mu$, for 83 s of continuous delivery, and this would be comparable in effect on the retina to 300 mW/sq. 10 $\mu$ for 83 s with a pulsed delivery of 100 ns every 15 $\mu$s, equivalent to an effective duty cycle of less than $\frac{1}{100,000}$.

The simplest yet very effective configuration that would allow this form of spatial modulation uses an imaging scanning laser 40 of 532 nm under AOM 44 control for the creation of a fixation target. The scanning laser 38 is replaced with the appropriate wavelength source for photodynamic therapy, and has an additional amplitude modulation or AOM control. The combination with the advanced graphics card 34 allows spatial modulation and synchronization as previously explained.

Although the description of the preferred embodiments for advanced spatial modulation of a therapeutic laser beam contains many specifications, these should not be construed as limiting the scope of the invention but as merely providing an illustration of the presently preferred embodiments of this invention. Other embodiments of the invention including additions, subtractions, deletions, or modifications of the disclosed embodiment will be obvious to those skilled in the art and are within the scope of the following claims. The scope of the invention should be determined by the appended claims and their legal equivalents, rather than by the examples given.

I claim:

1. A combination of a scanning laser ophthalmoscope and external therapeutic laser source, for delivering laser light to the retina of an eye comprising the elements of:
   A. said scanning laser ophthalmoscope, including a diagnostic laser source emitting a laser beam of a first wavelength, scanning means to create a first pivot point for said laser beam of a first wavelength, and first detecting means for generating video images of said retina with an electronic means of said scanning laser ophthalmoscope;
   B. a second diagnostic laser source emitting a laser beam of a second wavelength that is visible to said eye and is scanned through said pivot point, said scanning laser ophthalmoscope having further modulating means for said laser beam of a second wavelength for creating a fixation target visible to said eye;
   C. said therapeutic laser source and a fiber optic delivery means, emitting a laser beam of a third wavelength and having controlling means for size, polarization and intensity of said laser beam of a third wavelength;
   D. opto-mechanical means for coupling said scanning laser ophthalmoscope with said therapeutic laser source including a beam splitter, focusing means and structural support means, said beam splitter on which a coating is applied to permit said laser beam of a first wavelength, said laser beam of a second wavelength and said laser beam of a third wavelength to be combined before entering said eye, and said focusing means comprising a first optical means for collimating said laser beam of third wavelength and a second optical means for focusing said laser beam of a third wavelength onto said retina of said eye, and said structural support means calibrated to create a second pivot for said laser beam of a third wavelength, substantially coincident with said first pivot point of said scanning laser ophthalmoscope;
   E. second detecting means in said scanning laser ophthalmoscope comprising optical filter means for detecting by preference laser light of said third wavelength, said second detecting means generating video images of the impact of said laser light on said retina;
   F. image processing means comprising a computer and an imaging card capable of generating overlay graphics, said imaging card further including means for synchronizing the video images produced by said first and said second detecting means to timing signals provided by said electronic means of said scanning laser ophthalmoscope, and output means to document the location of said laser beam of a third wavelength on said retina;
   further including the improvement of a spatial modulator, said spatial modulator comprising a transmitting area for said laser light of said third wavelength and a blocking area for laser light of said third wavelength, said spatial modulator positioned in proximity of a confocal plane of said retina and said spatial modulator being transilluminated with said laser light of a third wavelength that is collimated by said first optical means of said focusing means, and subsequently focused onto said retina with said second optical means, said transmitting area conforming to a predetermined shape and size; thereby increasing the spatial selectivity of said therapeutic laser source when said laser beam of a third wavelength is applied to said retina of said eye.

2. The combination of a scanning laser ophthalmoscope and external therapeutic laser source, for delivering laser light to the retina of an eye according to claim 1, wherein said spatial modulator comprises a two-dimensional array of computer controlled addressable sub-units;
   thereby facilitating the creation of said transmitting area and said blocking area of said laser light of said third wavelength.

3. The combination of a scanning laser ophthalmoscope and external therapeutic laser source, for delivering laser light to the retina of an eye according to claim 1, further incorporating the improvement of an electro-mechanical transducer attached to said fiber optic delivery means, said electro-mechanical transducer transmitting vibrational energy to said fiber optic delivery means;
   whereby coherence and mode propagation are reduced in said laser light of said third wavelength and energy will be more evenly distributed onto said retina of said eye.

4. The combination of a scanning laser ophthalmoscope and external therapeutic laser source, for delivering laser light to the retina of an eye according to claim 1 wherein said second wavelength is more than one hundred nanometers separated from said third wavelength;
   thereby increasing the visibility of said fixation target when said therapeutic laser source is active.

5. A scanning laser ophthalmoscope for imaging the retina of an eye comprising the elements of:
   A. said scanning laser ophthalmoscope, including a diagnostic laser source emitting a laser beam of a first wavelength, scanning means to create a pivot point for said laser beam of a first wavelength, and detecting means for generating video images of said retina with an electronic means of said scanning laser ophthalmoscope;
   B. a second diagnostic laser source emitting a laser beam of a second wavelength that is visible to said eye and is scanned through said pivot point, said scanning laser ophthalmoscope having further modulating means for said laser beam of a second wavelength for creating a fixation target visible to said eye;
   C. image processing means comprising a computer, an imaging card capable of generating overlay graphics, and output means to document the location of said fixation target on said retina;
   further including the improvement of an adaptive optics lens, said adaptive optics lens attached to said scanning laser ophthalmoscope immediately in front of said eye, and said adaptive lens comprising an anterior and a posterior surface of such profile to neutralize previously determined wavefront aberrations of said eye;

whereby optimal conditions are created for imaging said retina using said fixation target and said pivot point as a reference.

6. A scanning laser ophthalmoscope for photodynamic therapy of the retina of an eye comprising the elements of:

A. said scanning laser ophthalmoscope, including a therapeutic laser source emitting a laser beam of a first wavelength, scanning means to create a pivot point for said laser beam of a first wavelength and a raster pattern onto said retina, and modulating means for adjusting the intensity of said laser beam of a first wavelength within said raster pattern;

B. a second diagnostic laser source emitting a laser beam of a second wavelength that is visible to said eye and is scanned through said pivot point, said scanning laser ophthalmoscope having further second modulating means for said laser beam of a second wavelength for creating a fixation target visible to said eye;

C. image processing means comprising a computer, an imaging card capable of generating overlay graphics, and output means to document the location of said fixation target and said laser beam of a first wavelength on said retina;

thereby increasing the spatial selectivity of said therapeutic laser source when said laser beam of a first wavelength is applied to said retina of said eye.

* * * * *